United States Patent [19]
Törmälä et al.

[11] Patent Number: 5,084,051
[45] Date of Patent: Jan. 28, 1992

[54] LAYERED SURGICAL BIOCOMPOSITE MATERIAL

[76] Inventors: Pertti Törmälä, Reikonkatu 7 C 7, SF-33730 Tampere; Seppo Vainionpää, Orapihlajatie 21-27 B 12, SF-00320 Helsinki; Pentti Rokkanen, Marjaniemenranta 29, SF-00930 Helsinki; Pertti Helevirta, Ojavainionkatu 10 A 4, SF-33710 Tampere; Marja Pellinen, Aaltosenkatu 31-33 C 24, SF-33500 Tampere, all of Finland

[21] Appl. No.: 215,010
[22] PCT Filed: Nov. 3, 1987
[86] PCT No.: PCT/FI87/00147
    § 371 Date: Aug. 24, 1988
    § 102(e) Date: Aug. 24, 1988
[87] PCT Pub. No.: WO88/03417
    PCT Pub. Date: May 19, 1988

[30] Foreign Application Priority Data
Nov. 3, 1986 [FI] Finland .................. 864457

[51] Int. Cl.⁵ .............................. A61F 2/00
[52] U.S. Cl. ........................ 606/77; 606/76; 623/13; 623/16; 428/688
[58] Field of Search .............. 623/16, 11, 13; 128/92 YP, 92 YQ, 92 YR; 428/688, 704; 427/2; 606/76, 77

[56] References Cited

U.S. PATENT DOCUMENTS

| | | | |
|---|---|---|---|
| 4,356,572 | 11/1982 | Guillemin et al. | 128/92 YQ X |
| 4,457,028 | 7/1984 | Draenert | 623/18 |
| 4,842,604 | 6/1989 | Dorman et al. | 623/16 |

FOREIGN PATENT DOCUMENTS

| | | | |
|---|---|---|---|
| 0011528 | 5/1980 | European Pat. Off. | 128/92 YR |
| 2412300 | 8/1979 | France | 128/92 YQ |

OTHER PUBLICATIONS

Higashi et al., "Polymer-hydroxy-apatite composites for biodegradable bone fillers", Biomaterials 1986, vol. 7, pp. 183-187, May 1986.

*Primary Examiner*—Randall L. Green
*Assistant Examiner*—Paul Prebilic
*Attorney, Agent, or Firm*—Pollock, Vande Sande & Priddy

[57] ABSTRACT

Biocomposite material that is especially suitable for bone surgical applications, containing:
at least one bioceramic piece (1) (bioceramic component) and
at least one material component (2).

The material component (2) comprises at least reinforcement elements which have been manufactured of essentially resorbable material like polymer, copolymer, polymer mixture and/or ceramic material.

7 Claims, 6 Drawing Sheets

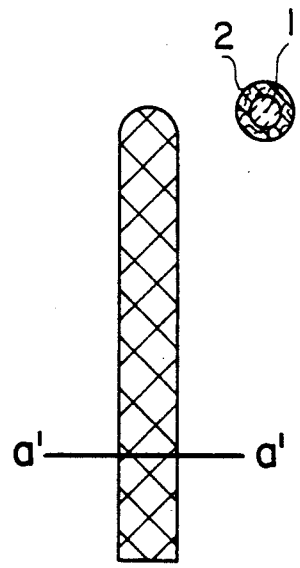
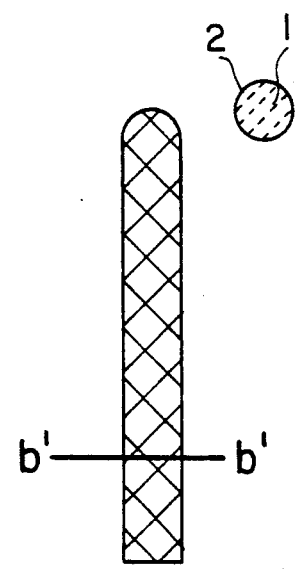
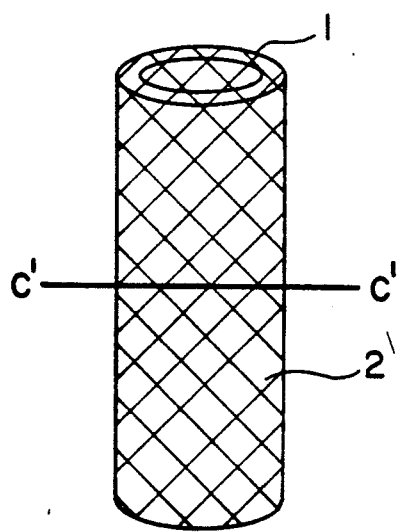
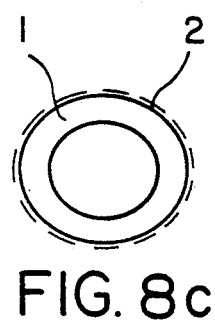

LAYERED SURGICAL BIOCOMPOSITE MATERIAL

BACKGROUND OF THE INVENTION

1. Technical Field

This invention describes a biocomposite material, which is especially suitable for bone surgical applications.

2. Background Art

It has been found that many ceramic materials have properties, which allow their use as bone graft materials. Ceramic materials (bioceramics), which are tissue compatible and/or which form chemical bonds with bone tissue and/or which promote the growth of bone tissue, are e.g. calcium phosphate: apatites such as hydroxyapatite, HA, $Ca_{10}(PO_4)_6(OH)_2$ (R. E. Luedemann et al., Second World Congress on Biomaterials (SWCB), Washington, D.C., 1984, p. 224), trade names such as Durapatite, Calcitite, Alveograf and Permagraft; fluoroapatites; tricalciumphosphates (TCP) (e.g. trade name Synthograft) and dicalciumphosphates (DCP); magnesium calcium phosphates, $\beta$-TCMP (A. Ruggeri et al., Europ. Congr. on Biomaterials (ECB), Bologna, Italy, 1986, Abstracts, p. 86); mixtures of HA and TCP (E. Gruendel et al., ECB, Bologna, Italy, 1986, Abstracts, p. 5, p. 32); aluminum oxide ceramics; bioglasses such as $SiO_2$-$CaO$-$Na_2O$-$P_2O_5$, e.g. Bioglass 45S (structure: $SiO_2$ 45 wt %, CaO 24.5%, $Na_2O$ 24,5% and $P_2O_5$ 6%) (C. S. Kucheria et al., SWBC, Washington, D.C., 1984, p. 214) and glass ceramics with apatites, e.g. MgO 4,6 wt %, CaO 44,9%, $SiO_2$ 34,2%, $P_2O_5$ 16,3% and CaF 0,5% (T. Kokubo et al., SWBC, Washington, D.C., 1984, p. 351) and calcium carbonate (F. Souyris et al., EBC, Bologna, Italy, 1986, Abstracts, p. 41).

The applications of the above ceramic materials as synthetic bone grafts have been studies by different means by using them for example both as porous and dense powder materials and as porous and dense macroscopical samples as bone grafts. Also ceramic powder-polymer composites have been studied in this way (e.g. W. Bonfield et al.. SWBC, Washington, D.C., 1984, p. 77).

Some bioceramics are resorbable like for example tricalciumphosphate (see e.g. P. S. Eggli et al., ECB, Bologna, Italy, 1986, p. 4) and calcium carbonate (F. Souyris et al., ibid, p. 41). The most known of the non-resorbable bioceramics is aluminum oxide. In literature it has been reported that some bioceramics, like hydroxyapatite, are both resorbable (W. Wagner et al., ECB, Bologna, Italy, 1986, Abstracts, p. 48) and non-resorbable (biostable) (e.g. G. Muratori, ibid, p. 64). Resorbable bioceramics dissolve in tissues slowly and/or they are replaced by the minerals of bone tissue. On the other hand, the biostable bioceramics remain in the tissues in an unchanged state, in such a way that the bone tissue grows into contact with the bioceramic.

Porosity of the bioceramic is advantageous, because the bone tissue can grow into the open porosity, if the pores have a suitable size. On the other hand, a problem of macroscopic bioceramic samples and especially of porous samples is their brittleness. It has been tried to compensate for the brittleness of bioceramics by manufacturing of ceramic powders and of biostable or of resorbable polymers composites, where the ceramic powder particles have been bound together by means of a polymer. This has been achieved e.g. by pressing the mixture of bioceramic powder and polymer powder by means of heat and pressure into a composite piece or by binding bioceramic powder by means of a reactive polymer to a composite piece. Such composites are tough when suitable polymers are applied. Composites of a bioceramic powder and resorbable polymer have been described e.g. in Finnish patent application 863573.

The ceramic powder-polymer composites have a disadvantage that the presence of binding polymeric material prevents the direct contact of bioceramic powder particles and bone tissue to each other, and therefore delays and prevents the growth of the bone tissue on the surface of composite material and inside of it, because the bone tissue does not have such an affinity to grow on the surface of biostable or resorbable organic polymers as it has to grow on the surface of bioceramics or into their internal open porosity. As a consequence the growth of new bone and the healing of tissue proceeds more slowly with bioceramic-polymer composites than with pure bioceramics (e.g. according to S. Ishida et al., ECB, Bologna, Italy, 1986, Abstracts, p. 86), the growth of new bone on the surface of 70% hydroxyapatite filler-triethyleneglycoldimethacrylate composite occurred in studies done with rabbits 2–3 times more slowly than the growth of new bone on the surface of pure sintered hydroxyapatite).

Bioceramics like hydroxyapatite are applied generally as bone graft materials in powder form for filling of bone defects or for alveolar ridge reconstruction by injecting the hydroxyapatite powder/water (or blood) mixture (particle size typically 10–50 mesh) on the bony surface of alveolar ridge into a cavity which has been done below the gingival tissue. The bone tissue grows rapidly into contact directly with hydroxyapatite particles, which when biostable remain as part of the forming new bone or are resorbed and replaced later with new bone.

The powder-like bone graft materials have, however, a disadvantage that they remain at their place only after the connective tissue and/or growing bone tissue binds them to their place. For example, in the case of hydroxyapatite powders applied for alveolar ridge augmentation this will take about one month. Before the powder particles have been bound to their place by means of tissue growth, the powder can move easily from the place, where it should be, when mechanical forces (e.g. biting) act upon the soft tissues which surround the powder particles. This can lead to a deterioration of good operation result or it is not achieved at all or it is achieved only partially.

The Finnish patent application 863473 and the corresponding PCT application FI87/00119 describe supporting structures which have been manufactured of resorbable polymer or composite and which can e applied to immobilize bioceramic particles to their place on the surface of bone. The applications of above invention have been restricted, however, surgically to such operations, where the bioceramic powder can be located on a certain restricted area which is surrounded by suitable tissues. The resorbable supporting structures of the above invention, like chute-like, box-like, flat tube or bag-like structures cannot be applied e.g. in the reconstructive surgery of flat bones of maxillofacial region or of skull. Additionally, the strength of the system comprising e.g. the chute or the corresponding and bioceramic powder is based only on the structure of the chute or the corresponding, when the bioceramic particles are not bound together by primary chemical bounds.

It has been found that bone tissue grows as a rule rapidly and without problems into bioceramic pieces which contain suitable open porosity. Because of the brittleness of these materials they can be, however, broken easily during operation or after it before the bone tissue has grown into the pore structure of ceramic material Also solid dense bioceramics are often brittle especially if they are thin, plate-like or curved pieces If the plate is broken during operation or soon after it the pieces of the plate can move in tissues and cause problems to the patient.

The strength, such as compression strength, of porous bioceramic pieces can be increased by coating the bioceramic sample with a resorbable or biostable polymer. The polymeric coating gives to the sample, however, only a limited increase of strength, because the strength of polymers is as a rule only moderate and the stiffness (the elastic modulus) is small in comparison to ceramics. Therefore, even small mechanical stresses can easily break the bioceramic part of composites manufactured of a porous bioceramic material and of a polymeric coating, because as a consequence of the small elastic modulus of polymer the external stresses are shifted already after small deformations to the ceramic component of the material.

EP-patent application 171884 describes an endoprosthetic device which comprises polyaryletherketone (PEEK) and possible additional biostable reinforcing fibres, such as carbon fibres, where the shifting of fibres into tissues can be prevented by means of a polymer-rich surface layer on the surface of the device. Further the above invention describes devices, which comprise a massive ceramic core component, which has been coated at least partially with tissue compatible biostable polymer. When the above devices are applied surgically, the biostable polymers and fibres remain permanently into the tissues of the patient and e.g. in the case of the application of ceramic block coated with a biostable polymer the polymer layer separates the ceramic core and the surrounding tissues permanently from each other preventing in this way the advantageous growth of surrounding tissues into direct contact with the ceramic block. In addition biostable polymers and fibres may release into surrounding tissues small particles, fibre fragments, or other debris as a consequence of wear, breakage or processing (see e.g. EP 171884, p. 14, lines 16–22). Small particles, fragments or debris cause as a rule in the surrounding tissues or in the nearby lymph nodes longlasting, even years lasting, foreign body and inflammation reaction.

SUMMARY OF INVENTION

In this invention we have found unexpectedly that when one manufactures a biocomposite pursuant to the present invention, one obtains a structure, which has the advantages of known bioceramics and bioceramic-polymer composites, but from which the problematic properties and weaknesses of the known materials have been mainly eliminated. In the materials of this invention there are combined to each other in surprising way the good mechanical properties of the material such as stiffness, toughness, strength and integrity) during operation and after it the desired period of time (at least the time which the safe healing demands) and also the easy and safe handling of specimen during operation.

The materials of this invention have as surprising advantages in comparison to the materials of EP 171884 (a) that the tissues which surround the biocomposite can be begin to grow immediately after the operation to direct contact with bioceramic component or into it through the open porosity of the material component or from the free surfaces of bioceramic component and (b) that after the resorption of material component the tissues which are in contact with the material component can grow also from this part advantageously into contact with bioceramic sample or also into its open porosity. Further for patients it is a surprising additional advantage that if biocomposite releases polymeric particles of fibre fragments they cause in the surrounding tissues or in the nearby lymph nodes only temporary reactions, because the cells of living tissues use these resorbable materials in their metabolism e.g. as nutrients.

The biomaterials of the invention describe an especially high improvement of mechanical properties in comparison to known bioceramic-polymer composites when the bioceramic component is coated at least partially by using as a coating agent continuous reinforcement fibre, reinforcement fibre bundle or a thread which has been constructed of short fibres or corresponding reinforcement structure, which may be coated with resorbable polymer and/or is wetted with polymer on the surface of bioceramic component. This reinforcement fibre, -bundle or thread can be installed on the surface of the bioceramic component e.g. by means of the filament winding method. The filament winding method is applied advantageously in such a way that the bioceramic component and/or the device which feeds the reinforcement fibre rotates at least around one axis and/or moves at least in the direction of one axis. The biocomposites of this invention manufactured by the above methods are even in case of porous bioceramic components so strong and tough (bending strength typically over 100 N/mm$^2$) that they can be applied in manufacturing of fixation devices of bone fractures (devices like rods, plates, intramedullary nails and so on). This is a surprising advantage because the known porous ceramics as such or as coated with nonreinforced polymers are too weak and brittle for such applications. When the surface of the bioceramic component of the biocomposite of this invention is at least partially free of polymeric material, and additional surprising advantage is the rapid fixation of biocomposite to the living tissues because of the rapid cell growth on the free surface of the bioceramic component and into its possible open porosity. When the open porosity of porous bioceramic component is at least partially free of the polymeric material, a surprising combination of good mechanical strength properties of the material, for patients secure handling of implants, rapid fixation of biocomposite with the living tissues and small loading of living tissues with resorbable foreign body material (resorbable polymer) is obtained.

When the biocomposite of the invention is manufactured of resorbable polymer component and of resorbable reinforcement elements one special advantage is that the polymer component and reinforcement elements are resorbed completely after the bioceramic has been reinforced sufficiently as a consequence of the cell growth on the surface of the bioceramic and/or into its open porosity.

This invention describes the above biocomposite materials, a method to manufacture them and their application as surgical implants e.g. to fill a defect, hole or corresponding in a bone, to augment the dimensions of the bone tissues, like in the case of the augmentation of alveolar ridges, to change the form of bone tissue in reconstructive surgery of maxillofacial bones or scull bones or in a corresponding meaning, or in fixation of bone fractures, osteotomies, arthrodesis or joint damages.

The material component of the biocomposites of the invention can contain resorbable thermoplastic or reactive thermosetting polymers, copolymers or polymer mixtures.

Resorbable polymers, copolymers and polymer mixtures are organic high molecular weight materials, which are depolymerized in tissue conditions by means of physicochemical hydrolysis and/or enzymatic activity. The material which is depolymerized to monomers or oligomers is removed from the living tissues by means of the normal metabolism of cells e.g. by means of energy production reactions or synthesis of protein molecules in the living cells. An advantage of surgical products and devices (implants) which are manufactured of resorbable polymers is the fact that they are removed from the living tissues after they have fulfilled their task without needing a separate removal operation, like the implants which are manufactured of biostable materials (e.g.—metals) often need.

Table 1 shows some important presently known resorbable polymers which can be applied in the biocomposites of this invention.

TABLE 1

Resorbable polymers which are suitable to biocomposites.

Polymer

Polyglycolide (PGA)
Copolymers of glycolide:
Glycolide/L-lactide copolymers (PGA/PLLA)
Glycolide/trimethylene carbonate copolymers (PGA/TMC)
Polyactides (PLA)
Stereocopolymers of PLA:
Poly-L-lactide (PLLA)
Poly-DL-lactide (PDLLA)
L-lactide/DL-lactide copolymers
Copolymers of PLA:
Lactide/tetramethylglycolide copolymers
Lactide/trimethylene carbonate copolymers
Lactide/δ-valerolactone copolymers
Lactide/ε-caprolactone copolymers
Polydepsipeptides
PLA/polyethylene oxide copolymers
Unsymmetrically 3,6-substituted poly-1,4-dioxane-2,5-diones
Poly-β-hydroxybutyrate (PHBA)
PHBA/β-hydroxyvalerate copolymers (PHBA/HVA)
Poly-β-hydroxypropionate (PHPA)
Poly-p-dioxanone (PDS)
Poly-δ-valerolactone
Poly-ε-caprolactone
Methylmethacrylate-N-vinyl pyrrolidone copolymers
Polyesteramides
Polyesters of oxalic acid
Polydihydropyrans
Polyalkyl-2-cyanoacrylates
Polyurethanes (PU)
Polyvinylalcohol (PVA)
Polypeptides
Poly-β-malic acid (PMLA)
Poly-β-alkanoic acids Reference: P. Tormala, S. Vainionpaa and P. Rokkanen in IVA's Beijer Symposium "Biomaterials and Biocompatibility," Stockholm, Sweden, August 25-26, 1987.

In addition to the above polymers there are a number of other polymers such as polymers of natural origin and modified polymers, which are at least partially resorbable in tissue conditions and which therefore can be applied according to this invention. Such polymers are for example collagen and its derivatives (Catgut), chitine polymers, gelatine (crosslinked gelatine) and cellulose derivatives (e.g. trade name Surgicel).

Several factors contribute to the resorption rate of resorbable polymers in physiological conditions. Such factors are e.g. the structure of polymer, the structure and form of the resorbable sample and the biological environment. The resorption rates of the resorbable polymers can vary in different cases from about one week to several years.

In the biocomposites of the invention can be used particularly well these resorbable polymers, copolymers or polymer mixtures or structures which are constructed of them, which retain at least part of their mechanical strength at least some weeks or months and are resorbed during several months or during a few years. With special caution one can use also polymers with more rapid resorption rates and on the other hand the use of polymers with more slow resorption rates does not cause as such disadvantages in surgical use.

One can apply in the biocomposites of this invention as a material component e.g. glass-, carbon-, aluminum oxide-, phosphate and other ceramic biostable or resorbable fibres, aramide-, polyester-, polyamide- and other biostable polymer fibres and/or resorbable polymer fibres like e.g. polylactide-, polyglycolide-, glycolide/lactide-copolymer-, polydioxanone-, poly-β-hydroxy butyrate-, glycolide/trimethylenecarbonate- or caprolactone fibres or other fibres which have been manufactured of polymers given in Table 1 or e.g. chitine polymer (chitosane fibres and above mentioned fibres bound together with some resorbable polymer, copolymer or polymer mixture.

It is self-evident to those skilled in the art that to the polymer and/or to the fibres can be mixed different additives which facilitate the processing or use of material or which modify the properties of the material. Such additives are e.g. colours, stabilizing agents or ceramic powders.

The ceramic of the biocomposite of this invention can be porous or nonporous ceramic block, which has been manufactured e.g. by sintering of ceramics given on side 1 such as of calcium phosphates, fluoroapatites, calcium carbonates, magnesium calcium phosphates, bioglasses, glass ceramics or of mixture of ceramics.

Biocomposites of this invention can be manufactured especially advantageously of bioceramics which have open porosity, but also nonporous bioceramics can become more secure for surgical use by combining them with resorbable reinforcement elements according to this invention.

It is advantageous that after the implant has been installed by surgical operation that the bioceramic component of biomaterial and the bone tissue have at least partially direct contact with each other in such a way that no other tissue or no other material (like e.g. binding polymer) does form between bioceramic component and bone tissue a completely continuous solid layer. When the bioceramic component and the bone tissue have a direct contact with each other one can obtain rapid, secure and safe filling and healing of a defect or of a hole in the bone or healing of bone reconstructed with biomaterial or healing of fracture, osteotomy or arthrodesis which has been fixed with biomaterial. When the above mentioned direct contact between bioceramic component of the implant and bone tissue exists the cells of the new bone can grow directly from the surface of the bone tissue rapidly close to the surface of the bioceramic (and also into the pores of bioceramic when it includes suitable open porosity; pore size e.g. the order of magnitude 200 μm). This guarantees the most rapid and best way for binding of bioceramic component and bone to each other and also for reinforcing the bioceramic component by means of cell growth into its pores.

When one applies known solid and porous bioceramics as bone surgical implant materials one obtains a good clear contact between bone tissue and bioceramic when a suitable bioceramic sample is located directly on the surface of the operated bone or into a hole, defect or corresponding in the bone. A problem of such known bioceramic samples is, however, the above mentioned brittleness, which cannot be eliminated merely by polymer coating.

It is possible to achieve also a good direct contact between bone tissue and bioceramic when one applies bioceramic powders as bone implants by locating the bioceramic powder on the surface of bone or into a defect, hole etc. in the bone. The disadvantages of powders are, however, the above-mentioned possibility of migration of powder particles and the absence of macroscopical mechanical properties of the powder. Also the application of a supporting structure, which surrounds at least partially the powder, is not suitable to some operations like to reconstruction of flat maxillofacial bones because the location of thin bioceramic powder layer (e.g. 1-6 mm layer) below a wide, low supporting structure (like a chute) is a difficult task.

One can manufacture thin, plate-like, curved or corresponding samples by binding bioceramic powder with biostable and/or resorbable polymer to a composite. However, the binding of bioceramic powder with biostable and/or resorbable polymer slackens the growth of new bone and the healing process. Such materials are often also too ductile to such fixations where high stiffness is needed (e.g. in the intramedullary nailing of fractures of long bones).

In using the biocomposites of this invention one can eliminate effectively all the problems of the above-mentioned known bioceramics and bioceramic-polymer composites by combining to each other macroscopical bioceramic samples (1) and essentially resorbable material components (2) which include reinforcement elements. The material components (2) of these biocomposites gives to them the toughness, strength and security of handling, because the strong and tough material component supports the brittle bioceramic component as a consequence of the high strength, toughness and high modulus of reinforcement elements. Therefore only very large external stresses can cause deformations in the bioceramic component.

On the other hand, the free surface, free surfaces or the parts of free surfaces of the bioceramic component make possible the rapid growth of bone tissue and its fixation to the composite. The resorbable polymer component (2) is resorbed advantageously later away,\when its supporting effect is not needed any more because the bone fracture, osteotomy or arthrodesis has been healed and/or the bone tissue has grown close to the ceramic component (and possibly into its open porosity). If one applies additionally biostable reinforcement fibres, they form after healing into the tissue an insert remnant.

The composites of this invention can be used in manufacturing to different surgical operations suitable macroscopical samples like plates, cubes, cylinders, tubes, chutes, rods or other samples with corresponding form and geometry. It is possible also to manufacture these composite samples which have the form of bones or parts of them and which samples can be applied e.g. in reconstructive bone surgery.

BRIEF DESCRIPTION OF THE DRAWINGS

FIGS. 8a'-8c' and 8a-8c show rod-like and tube-like biocomposite embodiments of the present invention.

BEST AND VARIOUS MODES FOR CARRYING OUT INVENTION

In the biocomposite of FIGS. 1-11 the bioceramic components (1) have been described as white, dotted regions and the reinforcement containing material components (2) as ruled regions (the ruling describes fibre reinforcement).

Figure 1A:
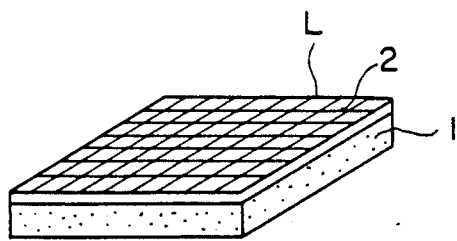
FIG. 1a shows a perspective view of a plate-like biocomposite sample.

FIG. 1a shows as a perspective figure a plate-like biocomposite sample which is formed of a plate-like bioceramic component (1) and of a polymer component (2) which is reinforced with a fabric which has been constructed of fibres (L) and which polymer component has been fixed on the surface of the bioceramic component.

It is natural that also other reinforcement element structures can be applied in this connection such as e.g. parallel fibres or fibres which are randomly oriented on the surface of the bioceramic (such as felts, non-woven gauches, short fibres etc.) and film-fibres. The reinforcing can be used in such a way that the reinforcement elements are located on the surface of the bioceramic components. Thereafter the reinforcement elements can be impregnated with monomer, oligomer, polymer or mixtures thereof by using techniques which are based on heating, pressures, solvents, radiation or catalytic reactions. The reinforcement elements can be located on the surface of the bioceramic component simultaneously with the polymer component. In every case as a consequence, a biocomposite is obtained, to which the fibre reinforcement of the material component (2) gives the unexpectedly high strength.

Figure 1B:
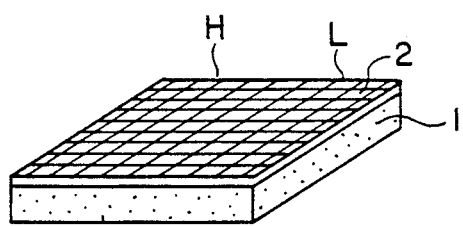
FIG. 1b shows an embodiment of FIG. 1a wherein layer (2) has pores or holes therethrough.

According to an advantageous embodiment the polymer component (2) contains open porosity or holes, through which the tissues above the polymer component can grow rapidly through the polymer component and to contact with the bioceramic component. Such a biocomposite is shown in FIG. 1b schematically. In this case the fibre reinforced (1) polymer component (2) contains holes or pores (H). Open porosity can be manufactured in the polymer component by applying typical methods which are known in the polymer technology such as by mixing with polymer, before manufacturing, a powdery soluble additive and then dissolving the additive away from the final biocomposite. One can also apply foaming agents in the polymer component to get open porosity.

Into the polymer component containing polymeric binding agents one can make bigger holes e.g. by working mechanically parts of the polymer component away by drilling or by milling. Holes are also obtained easily on the surface of material component (2) when part of the surface of bioceramic component (1) is left without coating or part of the surface of the bioceramic component is covered before coating with some kind of protective device and by removing the protective device after the coating of the biocomposite. The material component (2) of the biocomposite of the invention can be porous or it can contain holes because the fibre reinforcement gives to the biocomposite, good mechanical strength properties. This is achieved especially well when the reinforcement elements are continuous surrounding pores or holes. In such cases the reinforcement elements give a good reinforcement effect without preventing cell growth into the pores or holes.

The reinforcement element phase of the material component (2) of the invention may be manufactured essentially of resorbable material such as polymer, copolymer, polymer mixture and/or ceramic material and the possible binding material of the reinforced material component can be resorbable polymer, copolymer or polymer mixture. This polymer component may include also bioceramic powder which facilitates the growth of cells into the polymer component.

Figure 1C:
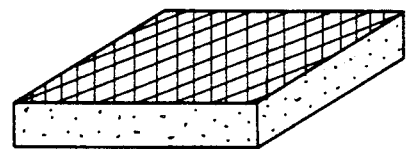
FIG. 1c shows an embodiment of FIG. 1a which has been manufactured by means of a filament winding method.

FIG. 1c shows a plate-like biocomposite of this invention, which has been manufactured by means of the filament winding method. This biocomposite comprises a bioceramic core and a reinforcement fibre layer which has been would on the surface of the bioceramic core. It is also possible to manufacture by filament winding such biocomposites where the material component (2) is porous when the reinforcement element fibres are wound on the surface of the ceramic core in such a way that between the reinforcement fibre bundles are left gaps (see e.g. FIG. 8c). Filament winding is an especially advantageous method to manufacture plate-like bioceramic samples, because such plates have optimal strength and stiffness properties and therefore such biomaterials can be applied in manufacturing of fixation plates for bone surgery.

Figure 2A:
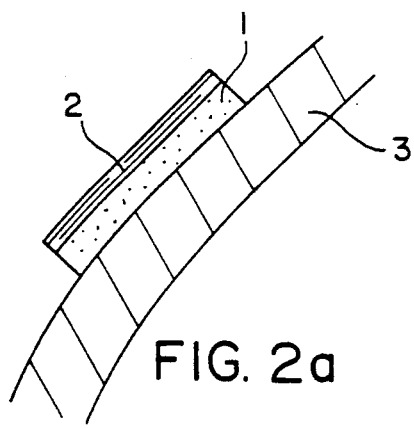
FIGS. 2a-2c show progressive steps of locating the plate-like composite on a bone surface and attaching it thereto.
Figure 2B:
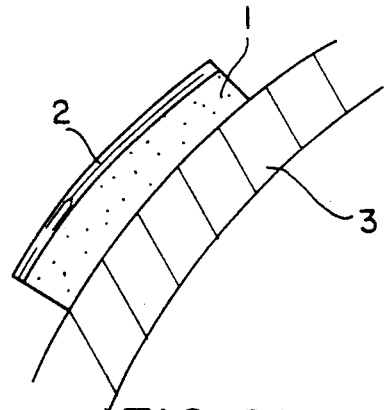
Figure 2C:
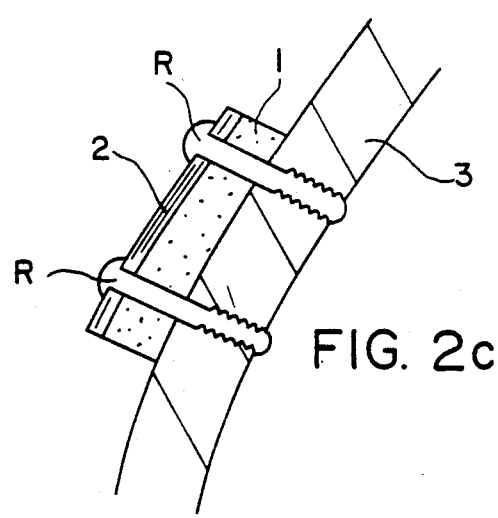

Such biocomposites as are described in FIGS. 1a–1c can be applied e.g. in reconstructive bone surgery. FIG. 2 shows schematically as a cross-section figure how the biocomposite sample is located on the surface of the bone tissue in such a way that the free lower surface of the bioceramic component (1) is located into contact or close to the surface (3) of the bone which will be reconstructed. This secures the rapid fixation of the biocomposite to the bone as a consequence of the growth of new bone tissue close to the bioceramic. If one applies a bioceramic component which contains open porosity it can be impregnated before operation or during operation with living autogenic cancellous bone which is sludged with blood or tissue fluids and which has been taken from some other bone of the patient (like the iliac crest). The living osteoblasts or preosteoblasts of such autogenic cancellous bone start reformation of new bone rapidly also into the open porosity of the bioceramic. It is possible also to impregnate the open porosity of the bioceramic with chemical additives which facilitate the cell-growth and/or with antibiotics to prevent the growth of micro-organisms inside of the bioceramic component. Depending on the form of the bone which shall be reconstructed (e.g. curved bone surfaces) one can manufacture curved or other plate-like composites (e.g. FIG. 2b).

The material component (2) gives to the biocomposite strength and toughness and it does not slacken or disturb significantly the growth of the new bone on the bioceramic or into its open porosity, because the polymer component according to FIGS. 1–2 is on the other side of the bioceramic component than the bone tissue to which the material is fixed.

The biocomposite can be fixed to bone e.g. with metallic or polymeric threads, screws, pins or corresponding. The biocomposite is an especially advantageous material for screw fixation. As a rule a brittle plate-like bioceramic cannot be fixed to bone by screws because it is broken easily during such an operation, but the tough reinforced material component (2) on the surface of the bioceramic component (1) makes possible the fixation of plate-like biocomposite with screws R to bone (3) such as is shown schematically in the cross-section FIG. 2c.

Figure 3:
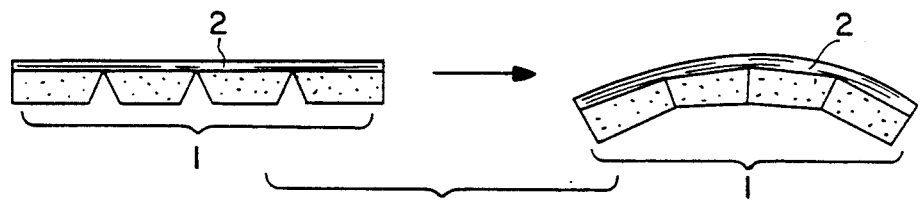
FIG. 3 shows the plate-like composite equipped with V-like grooves.

The tough material component (2) gives a surgeon the possibility to form the biocomposite during the operation. As an example the cross-sectional FIG. 3 shows how the bioceramic component (1) of biocomposite can be equipped with V-like grooves and how the biocomposite can be bent along these grooves because the tough polymer component can be deformed without breaking it. In this way the straight biocomposite sample can be changed to curved. Such a curved sample can then be fixed on the surface of the bone e.g. by screws.

Figure 4:
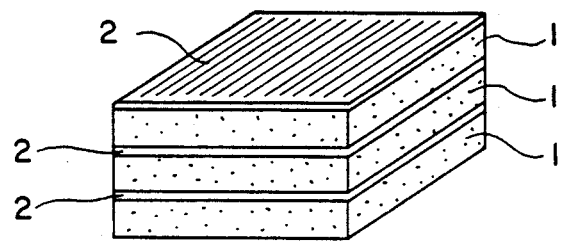
FIG. 4 shows plate-like composites stacked on top of one another.

Such plate-like biocomposite samples which are described in FIGS. 1–3 can be stacked as layered samples as is shown schematically in FIG. 4. In such stacked structures bioceramic components (1) and material components (2) can occur alternately. When one applies porous bioceramic components (1) and porous fibre reinforcement material components (2) it is possible to manufacture even big strong, tough bone grafts according to the FIG. 4.

Figure 5A:
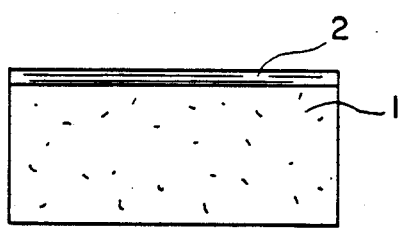
FIG. 5a shows a non-porous boundary component between layers (1) and (2).
Figure 5B:
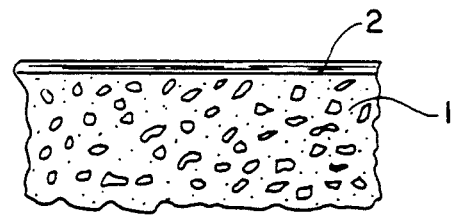
FIG. 5b shows a binding polymer penetrating layer (1).

When the biocomposite of the invention has been manufactured of non-porous bioceramic component the boundary surface between the bioceramic component (1) and material component (2) is pronounced when the material component (2) is located on the surface of the bioceramic component (1) as is shown schematically in the cross-sectional FIG. 5a. When the bioceramic component contains open porosity its boundary surface with the material component is a complicated three-dimensional network if the material component contains a binding polymer because the binding polymer penetrates during the manufacturing process of the biocomposite at least somewhat into the pore structure of the bioceramic. Such a case has been shown schematically in the cross-sectional FIG. 5b. The strength of the boundary surface and therefore also the strength of the whole biocomposite can be controlled by changing the penetration depth of polymer into the pores of the biocomposite.

Figure 6A:
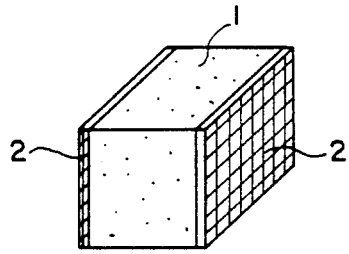
FIG. 6a shows a biocomposite where material components (2) have been affixed to two sides of bioceramic component (1).
Figure 6B:
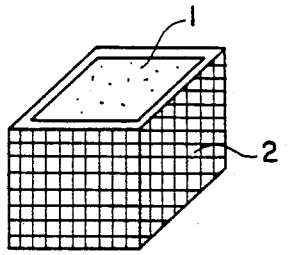
FIG. 6b shows a biocomposite where material components (2) have been affixed to four sides of bioceramic component (1).
Figure 6C:
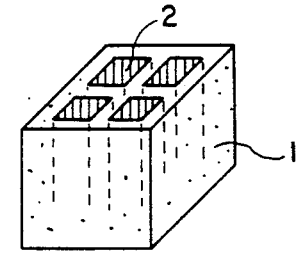
FIG. 6c shows a biocomposite reinforced internally with material components (2).

FIGS. 6a–6c show some cubic biocomposite samples of this invention. FIG. 6a shows a biocomposite where the material component layers (2) have been fixed on the opposite surfaces of the bioceramic sample (1). Such a material can be used to replace e.g. parts of flat bones. FIG. 6b shows a biocomposite where the cubic bioceramic piece (1) has been surrounded with a material component (2) in such a way that the upper and lower surfaces of the bioceramic piece are free. FIG. 6c shows a biocomposite, where the bioceramic piece (1) has been reinforced internally with one or several elongated material components (2).

FIG. 7 shows some cylindrical biocomposite samples of this invention. FIG. 7a shows a flat, cylindrical biocomposite sample, which comprises a bioceramic core (1) and a material component (2) which surrounds the bioceramic core like a hoop. It is advantageous to manufacture the hoop of totally resorbable polymeric material and reinforce it with resorbable fibres. The biocomposites of FIG. 7a can be applied e.g. as arthrodesis implants in operations of joints and vertebrae (see e.g. example 6). FIG. 7b shows a cylindrical biocomposite sample, which comprises an outer tube-like bioceramic component (1) and an inner cylindrical material component (2), which can also be hollow (tube-like) such as in the case of FIG. 7c. FIG. 7d shows a cylindrical biocomposite sample, which has been constructed of bioceramic-(2) and material components which are located within each other. The biocomposites of FIG. 7b–7d can be also applied as arthrodesis implants and also as fixation materials of bone fractures and osteotomies.

FIG. 8 shows some rod-like and tube-like biocomposites of the invention, which can be applied e.g. in fixation of long-bone fractures, as intramedullary nails and as fixation rods in treatment of cancellous bone fractures, osteotomies and arthrodesis.

FIG. 8a shows a non-porous bioceramic rod (1) which has been coated with fibre reinforced polymer (2). FIG. 8a shows the cross-section of this biocomposite in the plane a—a. The tough, reinforced material component on the surface of the bioceramic rod provides for excellent toughness- and strength properties. FIG. 8b shows a biocomposite rod, which comprises a bioceramic core (-components (1)) with open porosity and a fibre reinforced polymeric coating (-component (2)). Such a biocomposite rod is light, strong, tough and stiff as a consequence of this material combination. FIG. 8c shows a tube-like biocomposite sample, which consists of a tube-like bioceramic component (1) which advantageously contains open porosity and of a polymer-fibre composite (material component (2)) which has been wound on the bioceramic component. The winding is advantageously made in such a manner that between the wound fibre bundles openings remain such in the case of FIG. 8c. Polymer-fibre composite can be fixed on the surface of the bioceramic tube by feeding on the surface of the rotating bioceramic tube a fibre bundle which has been impregnated with a polymer. If one applies a reaction polymer (e.g. polyurethane) the polymer can be hardened only on the surface of the bioceramic tube, which leads to the fastening of the material component (2) on the surface of the bioceramic tube. If one applies a thermoplastic polymer the fibre bundle can be impregnated before winding with the solution of the polymer and the solvent can be evaporated when the fibre bundle is fastened on the surface of the bioceramic tube during winding. It is also possible to feed the fibre bundle through the melt of the thermoplastic polymer and to solidify polymer at the same time when the fibre bundle is wound on the surface of the bioceramic tube.

FIG. 9 shows some basic methods of filament winding (A=angle winding, B=radial winding, C=pole winding, D=weaving winding, E=multiaxial winding and F=circle winding (I. Airasmaa et al. "Lujitemuovitekniikka" (Reinforced plastics technology), Helsinki, 1984), which can be applied in manufacturing of the biocomposites of this invention. It is natural that also other filament winding methods than those shown in FIG. 9 can be applied in this connection.

In manufacturing of biocomposites of this invention it is possible to achieve the highest reinforcement element/binding polymer ratio when one applies the filament winding methods. The reinforcement elements can be directed optimally by changing the winding directions. Therefore the composites of FIG. 8c (e.g.—composites of 1c and corresponding materials) have many excellent properties. They are strong and tough because of the wound reinforced surface layer. They are light because of the hollow structure and of the porosity of the bioceramic component. The living tissues (bone- and other tissues) can grow rapidly into these biocomposites through the openings between the polymer-fibre bundles and further into the open porosity of the bioceramic tube. Such biocomposites can be applied e.g. in intramedullary nailing of long bones.

Figure 10:
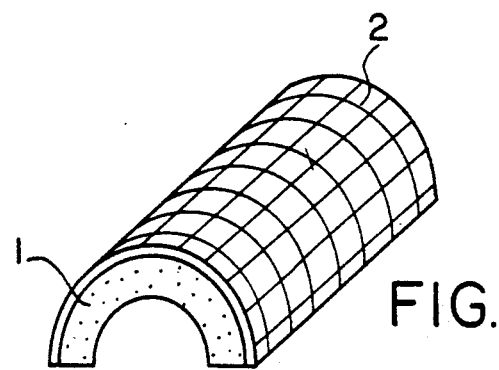
FIG. 10 shows a chute-like biocomposite.

FIG. 10 shows a chute-like biocomposite sample, which comprises a chute-like bioceramic component (1) and a reinforced material component (2) which has been laminated on the surface of the bioceramic component. Such biocomposites can be applied e.g. as replacements of parts of small tube-like bones.

Figure 11:
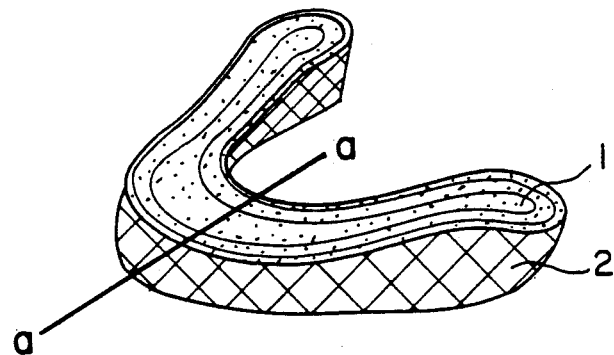
FIG. 11 shows a mandibular implant manufactured of a biocomposite of the present invention.
Figure 11A:
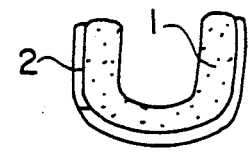
FIG. 11a is a cross-section of FIG. 11.

FIG. 11 shows a mandibular implant manufactured of a biocomposite of the invention. This mandibular implant consists of a bioceramic piece (1) which is of its cross-section a chute (FIG. 11a) and of a fibre reinforced material component (2) which is laminated on the outer surface of the bioceramic (1). The space inside of the chute can be filled advantageously e.g. with autogenic cancellous bone, with bioceramic powder (like with apatite) or with a mixture of bone and bioceramic powder, which facilitates the rapid ossification.

In the embodiments of FIGS. 1–11, can be applied nonporous or porous, biostable or resorbable bioceramic components and resorbable polymers in a nonporous or porous form, reinforcements like biostable and/or resorbable fibres, film-fibres or other reinforcement elements or structures which have been constructed of them.

It is advantageous to apply in fixation of bone fractures, osteotomies, arthrodesis or joint trauma biocomposites, where both bioceramic component and material component have been manufactured of resorbable materials. In such cases the whole biocomposite is resorbed and replaced by a new bone or another living tissues after the fixation effect of the biocomposite is not needed any more after the healing of the fracture, osteotomy, arthrodesis or the corresponding. In reconstructive surgery in filling bone defects, in changing the form of bone, in augmenting of bone etc. one can apply advantageously biocomposites, where at least the bioceramic component is biostable and tissue compatible and to which the cells of the growing bone tissue can be fixed.

It is self-evident for specialists that also other combinations of bioceramic components and material components than those shown in FIGS. 1-11 are possible and effective in use in surgery. For all biocomposites of this invention is a common feature, however, that the bioceramic component and the material component have at least one common boundary surface, through which the properties of the components are transmitted which gives strong, tough and secure biocomposites.

The following non-limiting examples illustrate the present invention.

EXAMPLE 1

Biocomposites which are described in FIG. 1 were manufactured of nonporous (S) (no significant open porosity) or of porous (P) (open porosity 20-70%) bioceramic plates (dimensions 30×10×4 mm) and of biostable or resorbable polymer reinforced with parallel fibres with the following methods:

(1) A large polymer film sample (the thickness about 2 mm) was located on the surface of the bioceramic piece (BP (on the 30×10 mm surface) so that the polymer film covered the whole surface of BP. The polymer film was pressed from above by means of a heated plate in such a way that the film melted and fixed tightly on the surface of BP. The thickness of the polymeric layer was then about 1 mm. The biocomposite piece was cooled under pressure.

(2) The reinforcement fibres were located on the surface of BP, a polymer film (the thickness about 2 mm) was placed on the reinforcement fibres and the film was compressed from above by means of a heated plate in such a way that the film melted, wetted the reinforcement fibres and penetrated to the surface of BP. The thickness of the material component (polymer and reinforcement) was then 1 mm and the weight fraction of the fibres about 40%. The biocomposite was cooled under pressure.

(3) The surface of BP was wetted with a polymer solution. The solvent was evaporated. This process was repeated so many times that a polymer layer with the thickness of 0.5 mm was obtained.

(4) The reinforcement fibres were placed on the surface of BP. The fibres and the surface of BP were wetted with the polymer solution. A microporous Teflon-film was compressed on the surface of the sample. The solvent was evaporated. The polymer solution process was repeated so many times that a polymer-fibre layer with the thickness of 0.5 mm was obtained (the weight fraction of the fibres=40%).

(5) The surface of BP was wetted with a reactive polymer system (with a monomer, oligomer or prepolymer or their mixture). A 1 mm thick layer of reactive polymer was obtained on the surface of BP.

(6) The reinforcement fibres were placed on the surface of BP. The fibres and the surface of BP were wetted with a reactive polymer system (a monomer liquid, oligomer, prepolymer or their mixture). A 1 mm thick layer of reaction polymer-fibre mixture (the weight fraction of fibres=40%) was cured on the surface of BP.

(7) The biocomposite was manufactured like above in the method (1), but the polymer film contained 60 w-% sodium chloride powder (the average particle size 100 μm). The biocomposite was immersed after manufacturing 6 h in distilled water at RT to dissolve the sodium chloride away. The biocomposite was dried, which gave a material with about 20 w-% of open porosity in its material component.

(8) The biocomposite was manufactured like above in the method (2) but in addition by using sodium chloride powder as a filler of the polymer film to achieve open porosity to the material component like above in the method (7).

(9) The biocomposite was manufactured like above in the method (3) but in addition by using in the polymer solution sodium chloride powder as an additive to achieve open porosity to the material component like above in the method (7).

(10) The biocomposite was manufactured like above in the method (4) but in addition by using in the polymer solution sodium chloride powder as an additive to achieve open porosity to the material component like above in the method (7).

(11) The biocomposite was manufactured like above in the method (5) but in addition by using in the reactive polymer system sodium chloride powder as an additive to achieve open porosity to the material component like above in the method (7).

(12) The biocomposite was manufactured like above in the method (6) but in addition by using in the reactive polymer system as an additive sodium chloride powder to achieve open porosity to the material component like above in the method (7).

Figure 12:
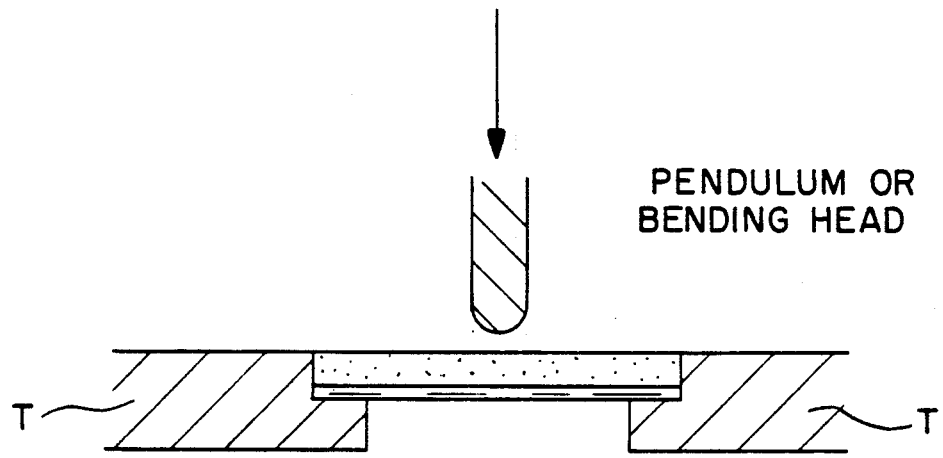
FIG. 12 schematically shows a testing arrangement for measuring the impact and bending strengths of the composites of the present invention.

The impact- and the bending strengths of the above composites were measured by means of the device and arrangement shown schematically in FIG. 12. The biocomposite sample (BP) was fixed of its both ends into a supporting bench (T). The basic principle of the impact strength measurement was to allow a pendulum of known mass to fall through a known height and strike the specimen at the lowest point of its swing and to record the height to which the pendulum continued its swing. The bending strength was measured by bending a biocomposite sample to its fracture with a constant speed (10 mm/min) by a moving bending head from the middle of the sample according to FIG. 12. The impact strength was calculated as the absorption of impact energy divided with the cross-sectional area of the sample. The bending strength was calculated as the maximum bending load carrying capacity of the sample in relation to its cross-sectional area. More accurate information of the arrangements of impact and bending measurements is given e.g. in the following book: Handbook of Plastics Test Methods, R. P. Brown (ed.), George Godwin Limited, London, Great Britain, 1981, Chapter 8. As reference values were used the impact and bending strength values which were measured with the identical measurement arrangements for the pure bioceramic pieces.

Table 2 shows components and manufacturing method of some studies hydroxyapatite (HA)+polymer systems and HA+polymer composite systems (polymer+carbon fibre 40 w-%). Table 3 shows the relative minimum and maximum impact strength and bending strength values of the studied composites (the strength values divided with strength values of the corresponding HA).

TABLE 2

Some biocomposites and their manufacturing methods. Four different biocomposites were manufactured of every polymer; Samples 1, 5, 9 etc.: porous HA + polymer, samples 2, 6, 10 etc.: porous HA + polymer-carbon fibres (40 w-% fibres), samples 3, 7, 11 etc.: nonporous HA + polymer, samples 4, 8, 12 etc.: nonporous HA + polymer + carbon fibres.

| Sample N:o | Polymer | (3) Manufacturing methods of samples (N:o) |
|---|---|---|
| 1–4 | High density polyethylene (HDPE) | 1, 2 |
| 5–8 | Polypropylene (PP) | 1, 2 |
| 9–12 | Polystyrene O—2 | |
| 13–16 | Styreneacrylnitrile copolymer (SAN) | 1, 2 |
| 17–20 | Epoxide (EP) | 5, 6 |
| 21–24 | Polyamide (PA) | 1, 2 |
| 25–28 | Polyoximethylene (POM) | 1, 2 |
| 29–32 | Phenylene oxide (PPO) | 1, 2 |
| 33–36 | Polycarbonate (PC) | 1, 2 |
| 37–40 | (1) Polymethylmethacrylate (PMMA) | 5, 6 |
| 41–44 | Polytetrafluoroethylene (PTFE) | 1, 2 |
| 45–48 | Polysilicone (PSi) | 1, 2 |
| 49–52 5, 6 | Polyurethane | |
| 53–56 | Polyarylate (PAr) | 1, 2 |
| 57–60 | Polyetheretherketone (PEEK) | 1, 2 |
| 61–64 | Polyester (PES) | 1, 2 |
| 65–68 | Polyphelyne sulphide (PPS) | 1, 2 |
| 69–72 | Polysulphone (PSu) | 1, 2 |
| 73–76 | Polyethyleneterephthalate (PET) | 1, 2 |
| 77–80 | Polyglycolide (PGA) | 1, 2 |
| 81–84 | Poly-L-lactide (PLLA) | 1, 2 |
| 85–88 | Poly-DL-lactide (PDLLA) | 3, 4 |
| 89–92 | Glycolide/lactide copolymer (PGA/PLA) | 1, 2 |
| 93–96 | Glycolide/trimethylenecarbonate copolymer (PGA/TMC) | 1, 2 |
| 97–100 | Polyhydroxybutyrate (PHBA) | 3, 4 |
| 101–104 | Hydroxybutyrate/hydroxyvalerate copolymer (PHBA/PHVA) | 1, 2 |
| 105–108 | Poly-p-dioxanone (PDS) | 3, 4 |
| 109–112 | (2) Polyesteramide (PEA) | 1, 2 |
| 113–116 | Poly-e-caprolactone | 1, 2 |
| 117–120 | Poly-d-valerolactone | 1, 2 |
| 121–128 | Polyetherester | 1, 2 |
| 125–128 | Chitine polymer | 3, 4 |

(1) Bone cement
(2) The structural formula of polymer:

(3) In the case of every polymer the first manufacturing method was applied to do nonreinforced samples and the second method to do fibre reinforced samples.

TABLE 3

| The strength regions of biocomposites of Table 2. | | |
|---|---|---|
| Material | Relative impact strengths | Relative bending strengths |
| Porous HA + polymer | 3.5–40 | 1.1–2 |
| Porous HA + reinforced polymer | 120–240 | 1.6–6 |
| Nonporous HA + polymer | 1.1–4.2 | 1.1–1.6 |
| Nonporous HA + reinforced polymer | 1.8–20 | 1.1–3.5 |

It was found that the strengths of all fibre reinforced composites were clearly better than the strengths of HA or of HA coated only with a polymer.

EXAMPLE 2

The manufacturing method (2) of example 1 was applied to manufacture biocomposites shown schematically in FIG. 1a. The used materials were: nonporous (S) and porous (P) (open porosity 20–70%) bioceramic plates (dimensions 30×10×4 mm) and resorbable polymer composites. Table 4 shows some mechanical strength measurement values for biocomposites where hydroxyapatite ceramics were applied as bioceramic components. The relative impact and bending strength values of biocomposites were obtained by dividing the strength values of biocomposites with the corresponding strength values of pure hydroxyapatite bioceramics.

TABLE 4

| | Properties of biocomposites. | | | [5]The relative strength of the biocomposite | |
|---|---|---|---|---|---|
| Sample N:o | Bioceramic component | Polymer component | Reinforcement fibres of polymer component | Impact strength | Bending strength |
| 1, 2 | HA: [1]P and [2](S) | PGA | PGA | [3]120  [4](20) | [3]3  [4](1.4) |
| 3, 4 | " | PLLA | PGA | 110  (32) | 3.2  (1.8) |
| 5, 6 | " | PDLLA | PLLA | 140  (40) | 2.8  (2.0) |
| 7, 8 | " | PHBA | PGA | 135  (35) | 2.6  (1.8) |
| 9, 10 | " | PDS | PGA | 200  (65) | 2.1  (1.6) |
| 11, 12 | " | PDS | PLLA | 220  (80) | 2.2  (1.8) |
| 13, 14 | " | PEA | PLLA | 185  (65) | 1.8  (2.0) |

[1]Porous (open porosity about 60%)
[2]Nonporous (no significant open porosity)
[3]The values of biocomposites containing porous bioceramic components
[4]The values of biocomposites containing nonporous bioceramic components
[5]The thickness of the reinforced material component about 0.4 mm Several porous bioceramics (porosity 40–70%) and the polymers and fibre reinforcements of Table 4 were applied to manufacture corresponding biocomposites to those shown in Table 4. The following bioceramics were used: tricalcium phosphate, dicalcium phosphate, magnesium/calcium-phosphate, fluoroapatite, aluminum oxide and calcium carbonate. The relative impact strengths of these biocomposites varied between 85 and 220 and the relative bending strengths between 1.4 and 3.8. When the corresponding composites were manufactured without fibre reinforcement of the polymer component the strength values varied between 2 and 12 (the relative impact strength) and between 1.0 and 1.6 (the relative bending strength).

EXAMPLE 3

A bioceramic piece with dimensions of 30×10×3 mm was placed into an injection moulding mould (the dimensions of the inner cavity of the mould were 30×10×4 mm). The empty space (30×10×1 mm) inside of the mould cavity above the bioceramic sample was filled with a melt of liquid crystalline thermoplastic polymer (manufacturer Celanese Inc., trade name Vectra: injection moulding quality) in such a way that the polymer melt filled the empty space of the mould and was fixed to the bioceramic piece. The mould was cooled and opened and a biocomposite sample with dimensions of 30×10×4 mm was obtained with a bioceramic component and the liquid crystalline polymer component.

Following bioceramics were applied in manufacturing biocomposites: hydroxyapatite (nonporous and porous materials), fluoroapatite, tricalcium phosphate dicalciumphosphate, magnesium calcium phosphate, an alloy of hydroxyapatite and tricalcium phosphates, aluminum oxide, bioglass 45S, a glass ceramic containing apatite ($MgO-CaO-SiO_2-P_2O_5-CaF$) and $CaCO_3$. The porosities of bioceramics were between 20 and 70% in the different cases.

The relative impact and bending strengths of the above biocomposites were measured according to Example 1 and FIG. 12. In the case of biocomposites containing porous bioceramic components the relative impact strengths were between 80 and 180 and the relative bending strengths between 3 and 8. The materials containing solid bioceramic components showed the relative impact strengths 6–30 and the relative bending strengths 1.4–2.4.

EXAMPLE 4

Porous calcium carbonate ($CaCO_3$) pieces (porosity about 70%, the dimensions 40×12×12 mm) were applied to manufacture according to the methods 3 (and 4) of Example 1 biocomposites whose principal structure is given in FIG. 1. The following biocomposites were manufactured: Sample 1=pure $CaCO_3$, Sample 2=$CaCO_3$ whose one long surface is coated with 0.5 mm thick layer of PLLA ($M_W$=260 000), Sample 3=$CaCO_3$+one long surface is coated with 0.5 mm thick layer of PDS, Sample 4=$CaCO_3$+one long surface is coated with 1 mm thick layer of PDS which is reinforced with 0.5 mm thick PGA/PLLA fibre fabric (the fibre content of polymeric material component=40 vol.-%), Sample 5=like Sample 4 but all the long surface of the $CaCO_3$ piece are coated with the fabric, Sample 6=filament wound sample: $CaCO_3$ piece was coated by winding on it 0.5 mm thick layer of PLLA fibres coated with PDLLA (the winding temperature 150° C., the thickness of fibre bundle=0.1 mm, the amount of filament wound layers of fibre bundles on the surface of bioceramic was 5), Sample 7=filament wound sample like Sample 6 but noncoated PLLA fibres were applied as reinforcing material component.

Table 5 shows the relative strength values of Samples 1–7 when compared to the strength values of pure $CaCO_3$.

TABLE 5

| The relative strengths of Samples 1–7. | | |
|---|---|---|
| Sample N:o | Impact Strength | Bending strength |
| 1 | 1 | 1 |
| 2 | 2 | 1.8 |
| 3 | 2.4 | 1.4 |
| 4 | 190 | 2.2 |
| 5 | 460 | 9.5 |
| 6 | 800 | 35 |
| 7 | 560 | 2.0 |

EXAMPLE 5

Biocomposites whose structure is given principally in FIG. 1b were manufactured according to the method (4) of Example 1 of porous hydroxyapatite (open porosity 60%) and of PLLA, which was reinforced with different biostable fibres (the fraction of fibres in comparison to PLLA 40%). Table 6 shows the applied reinforcement fibres and the relative impact strengths of biocomposites (when compared to the impact strength of porous HA).

TABLE 6

| The relative impact strengths of HA-PLLA-fibre composites | | |
|---|---|---|
| Sample N:o | Reinforcement fibres of material component | Relative impact strengths |
| 1 | E-glass fibres | 220 |
| 2 | Carbon fibres | 160 |
| 3 | Aramide fibres | 380 |
| 4 | Aromatic polyester fibres | 400 |

EXAMPLE 6

Figure 7A:
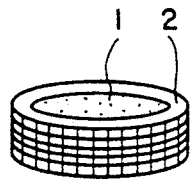
FIGS. 7a-7d show cylindrical biocomposite samples of the invention.

Cylindrical biocomposite samples whose structure is given principally in FIG. 7a were manufactured of porous hydroxyapatite (HA) (sample dimensions: height 3 mm, diameter 6 mm, degree of porosity 50%), of polylactide polymer and of polylactide reinforcement fibres in the following manner.

PLLA fibre bundles coated with PDLLA melt were wound rapidly on the cylindrical surface of HA-cylinders so that a homogenous PLLA fibre reinforced PDLLA coating was achieved on the cylindrical surface of HA-pieces. The upper and lower surfaces of biocomposite cylinders were left free. The cylindrical biocomposite samples were implanted between vertebrae C3-4, C4-5 or C5-6 of rabbits to replace the intervertebral discs. Normal aseptic operation techniques were applied. The movement of biocomposite plates was prevented anteriorly be means of resorbable sutures which were tightened between the vertebrae. Altogether 22 implants were implanted in 14 rabbits. The position of implants and the progress of fusion was followed radiographically in three weeks periods. As a reference series were six rabbits, into which were implanted nine porous HA-cylinders without reinforced polymeric surface layer.

During the implantation of the biocomposites of this invention the operations proceeded without problems and all the implantations healed in a good or satisfactory manner without any radiographical observation of breaking of biocomposite cylinders or any significant partial extrusion of samples from the intervertebral space.

In the reference series two HA-cylinders were broken during implantation operation, several cylinders were broken during healing and were extruded at least partially from the intervertebral space into the surrounding soft tissue. This showed clearly the surprising advantages of the biocomposite of this invention in comparison to the pure HA-cylinder.

EXAMPLE 7

Figure 7B:
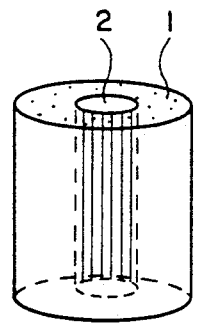
Figure 7C:
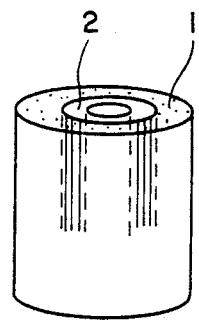
Figure 7D:
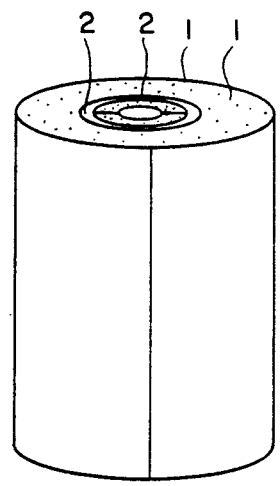
Figure 9A:
FIGS. 9A-9F show basic methods of filament winding to form biocomposites of the present invention.
Figure 9E:
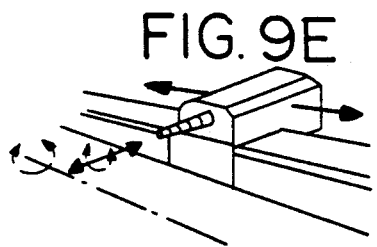
Figure 9B:
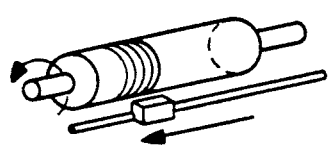
Figure 9D:
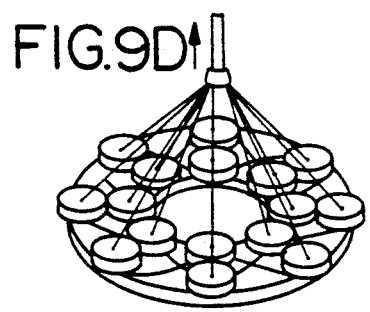
Figure 9C:
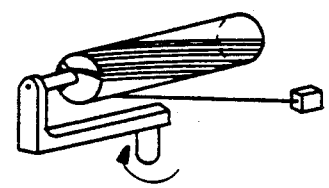
Figure 9F:
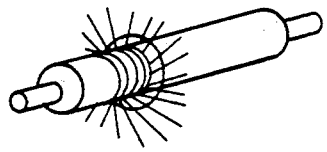

Cylindrical, layered biocomposites whose structure is given schematically in FIG. 7b were manufactured of porous (porosity about 50%) hydroxyapatite (HA) tubes (length 30 mm, outer diameter 2.6 mm, inner diameter 1.6 mm) by filling the inner cavity of tubes with polymer components in the following way:

(1) The inner cavity of the tube (Layer 2) was filled with the polymer melt (Layer 1) by melt moulding and the biocomposite was cooled.

(2) The self-reinforced resorbable polymer composite rod or the polymer composite rod reinforced with biostable fibres was immersed in a solution of resorbable polymer (10% w/v solution) and the rod was tapped rapidly into HA-tube and the biocomposite was dried. The dimensions of rods were: diameter 1.5 mm, length 30 mm.

(3) The biocomposite rods which were manufactured with the above method (2) were coated with resorbable polymer (Layer 3) by immersing the biocomposite rods into a solution of resorbable polymer (>5% w/v solution) and by drying the samples. This operation was repeated so many times that the resorbable surface layer with thickness of 0.1 mm was achieved.

(4) Biocomposite rods of the above method (2) were coated with a solution of resorbable polymer (5% w/v solution) which contained sodium chloride powder (average particle size 100 μm) so that the amount of sodium chloride powder was about 40 w-% of the weight of the dry polymer. The rods were coated with 0.15 mm thick polymer-sodium chloride layer. The solvents were evaporated in vacuum. The sodium chloride was dissolved in distilled water and the biocomposite rods were dried. Accordingly, these polymer composite rods comprised of a surface layer of resorbable polymer with open porosity, of a porous HA-tube and of a self-reinforced core inside of the HA-tube.

Table 7 shows the relative impact and bending strength values of the manufactured biocomposite rods in comparison to the corresponding strength values of HA-tubes.

TABLE 7

The relative strength values of cylindrical biocomposites.

| Sample N:o | Manuf. method (Ex. 7) | Layer 1 | Layer 2 | Layer 3 | Relative strengths Impact strength | Bending strength |
|---|---|---|---|---|---|---|
| 1 | — | — | HA | — | 1 | 1 |
| 2 | 1 | HDPE | " | — | 35 | 16 |
| 3 | 2 | self-reinf. PLLA | " | — | 180 | 60 |
| 4 | 3 | self-reinf. PLLA | " | PLLA | 230 | 65 |
| 5 | 4 | self-reinf. PLLA | " | " | 195 | 65 |

EXAMPLE 8

Biocomposite rods of Table 7 (Samples 1-5) were manufactured according to Example 7. Additionally cylindrical rods with length 30 mm, diameter 2.6 mm were injection moulded of PLLA containing 30 w-% HA-powder (particle size between 10 μm and (200 μm) (Sample N:o 6). The samples were located in mandibles of rabbits between both sides of ostectomized inferior border of the mandible through the soft tissues under the mylohyoid muscle. The porous HA-tubes (Sample 1) were broken easily during operation and part of them was broken also during the early follow-up period after the operation (during one week after operation). All the biocomposite samples and Sample N:o remained unbroken during the operation and during the follow-up (6 months).

Padiographic studies showed new bone formation along the surfaces of the implanted materials and into their possible open porosity from both sides of ostectomized mandible. Clear variations in osteoconductivity of different materials could be seen because the growth rates of new bone on the surfaces of the rods had the following order:

| rapid | | | | | slow |
|---|---|---|---|---|---|
| Sample 1 = | Sample 2 = | Sample 3 > | Sample 5 > | Sample 6 > | Sample 4 |

EXAMPLE 9

Following bioceramics were applied to manufacture porous (open porosity 40-60%) and nonporous, thin, plate-like samples (dimension 20×5×1 mm): hydroxyapatite, tricalcium phosphate, dicalcium phosphate, aluminum oxide, bioglass (Bioglass 45S) and calcium carbonate. The plates were coated with PLLA, which contained 40 w-% of biostable glass fibres (E-glass) or biodegradable glass fibres (calcium phosphate fibres) as reinforcing elements (plates were made as in Example 1, method 4). The relative impact strengths of biocomposites were 80-600 and 30-200 in the case of biocomposites with porous and nonporous bioceramic components respectively. The corresponding relative bending strengths of biocomposites were 15-40 and 1.2-4 in comparison to the strength values of corresponding porous and nonporous bioceramic components, respectively.

EXAMPLE 10

Porous hydroxyapatite (HA) tubes (open porosity about 50%, the outer diameter 11 mm, the inner diameter 9 mm and the length 60 mm) were coated by filament winding with PLLA fibre bundle which was coated with PDLLA. The thickness of the fibre bundle was 0.1 mm. PDLLA/PLLA relation was 50/50. The fibre bundles were wound on the tubes according to the principles of FIG. 8c at about 150° C. temperature. The thickness of the reinforced polymeric coating was 2 mm. The surface of the coating was compressed smooth in a cylindrical heated mould.

Corresponding coated HA-tubes were manufactured by melt moulding on the HA-tubes 2 mm thick layers of PDLLA polymer in an injection moulding mould. The impact and bending strengths were measured 1) for HA-tubes, 2) for PDLLA-coated HA-tubes and 3) for PDLLA/PLLA (fibre reinforcement)-coated HA-tubes. Table 8 shows the relative strength values.

TABLE 8

Relative strength values of HA-tubes and HA-PLA-composite materials.

| Sample N:o | Material | Relative strength values Impact str. | Bending str. |
|---|---|---|---|
| 1 | HA-tube | 1 | 1 |
| 2 | PDLLA-coated HA-tube | 50 | 8 |
| 3 | PDLLA/PLLA (fibre reinforcement)-coated HA-tube | 760 | 75 |

What is claimed is:

1. Biocomposite material for bone surgical applications, which biocomposite comprises:

at least one bioceramic layered component and at least one material component layer which has been manufactured of at least one polymer which material component has at least one common boundary surface with the bioceramic component; wherein the material component comprises at least reinforcement elements which have been manufactured of resorbable material selected from the group consisting of polymer, copolymer, polymer mixture, and ceramic material and mixtures thereof and that the material component can include binding material which is manufactured of resorbable polymer, copolymer or polymer mixture and that whereby the material component is porous at least in tissue conditions, and wherein the bioceramic component is at least partially porous and that the material component has a surface contact connection with the bioceramic component in such a way that the part of the porosity of the bioceramic component, which is to be put against the bone tissue, is free of the material component.

2. A biocomposite material according to claim 1, wherein the reinforcement elements are fibres or film fibres or structures which have been constructed of them, which reinforcement elements have been manufactured from the resorbable polymers selected from the group consisting of polyglycolides (PGA), polyactides (PLA), glycolide/lactide copolymers (PGA/PLA), glycolide/trimethylenecarbonate copolymers (PGA/TMC), poly-$\beta$-hydroxybutyric acid (PHBA), poly-$\beta$-hydroxypropionic acid (PHPA), poly-$\beta$-hydroxyvaleric acid (PHVA), PHBA/PHVA copolymers, poly-p-dioxanone (PDS), poly-1,4-dioxanone-2,5-diones, polyesteramides (PEA), poly-$\epsilon$-caprolactone, poly-$\delta$-valerolactone, polycarbonates, polyesters of oxalic acids, glycolic esters, dihydropyrane polymers, polyetheresters, cyanacrylates or chitine polymers.

3. A biocomposite material according to claim 1, wherein the binding material of the material component has been manufactured from resorbable polymers selected from the group consisting of polyglycolides (PGA), polylactides (PLA), glycolide/lactide copolymers (PGA/PLA), glycolide/timethylenecarbonate copolymers (PGA/TMC), poly-$\beta$-hydroxybutyric acid (PHBA), poly-$\beta$-hydroxypropionic acid (PHPA), poly-$\beta$-hydroxyvaleric acid (PHVA), PHBA/PHVA copolymers, poly-p-dioxanone (PDS), poly-1,4-dioxanone-2,5-diones, polyesteramides (PEA), poly-$\epsilon$-caprolactone, poly-$\delta$-valerolactone, polycarbonates, polyesters of oxalic acid, glycolic esters, dihydropyrane polymers, polyetheresters, cyanoacrylates or chitine polymers.

4. A biocomposite material according to claim 1, wherein the bioceramic component has been manufactured bioceramics selected from the group consisting of calciumphosphates, dicalciumphosphates, apatites and magnesiumcalciumphosphates, mixtures of hydroxyapatite and tricalciumphosphate, aluminiumoxide ceramics, bioglasses, glass ceramics containing apatites or calciumcarbonate.

5. A biocomposite material according to claim 1, wherein the bioceramic component of the biocomposite is a plate, a rod, a prism, a cylinder, a tube or a chute or it has been designed to correspond anatomically some bone or some part of a bone and that the material component has been located on at least one surface of the bioceramic component.

6. A biocomposite material according to claim 1, wherein in that the biocompatible material comprises a bioceramic component in the form of a plate, whose upper-or lower surface or side surfaces have been coated with material component.

7. A biocomposite material according to claim 6, wherein the biocomposite material has been organized to a layered sample, where the bioceramic components and material components alternate.

* * * * *